United States Patent [19]

McRae

[11] Patent Number: Plant 6,375

[45] Date of Patent: Nov. 8, 1988

[54] LILY PLANT NAMED 'RED SONG'

[75] Inventor: Edward A. McRae, Boring, Oreg.

[73] Assignee: Melridge, Inc., Aurora, Oreg.

[21] Appl. No.: 929,325

[22] Filed: Nov. 10, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid lily plant bearing clusters of large flowers on a tall stem, particularly distinguished by their deep red coloration, even in the bud stage, the glossy sheen of their upper tepals and by their inconspicuous spotting, the flowers being of excellent form and long persistence both on the plant and as cut flowers. This combination is completely new in the upright Asiatic divisions of lilies suited to forcing and to mass commercial cultivation. The plant is an excellent garden plant and is highly resistant to disease showing high tolerance of virus. The bulbs may be precooled and forced for cut flower production and the clone is vigorous and is a good grower and propagator.

1 Drawing Sheet

BACKGROUND OF THE INVENTION

This new variety of lily plant originated as a seedling selected from a group of seedlings planted by me at Sandy, Oreg., and resulting from crossing of the clonal cultivar 'Connecticut Red' as the seed parent with the clonal cultivar 'Lovesong' (U.S. Plant Pat. No. 4,178). The objective of this crossing was the production of lilies in shades of red well suited to forcing for cut flower production out of season, heretofore unknown in the lily breeding art, and the selected seedling appeared to me to be a satisfactory example of my said objective.

The flowers of this new lily are characterized by large size, broad tepalled form, upright orientation, and a rich, deep red color accented by a glossy sheen, thereby providing a color pattern unique in this type of lily. This selected seedling was asexually reproduced by me at Sandy, Oreg., with such satisfactory results that extensive reproduction was carried on under my direction at Sandy, Oreg., through successive generations by bulb scale propagation and by natural propagation from bulblets, which demonstrated that the novel and distinctive characteristics of this new variety would hold true under asexual propagation from generation to generation and appeared to be firmly fixed. This new plant has been found to be well suited to forcing out of season when the bulbs are dug at the appropriate time and properly precooled; October-dug bulbs, properly precooled and potted in January, will flower under glass in Western Oregon, with no supplementary lighting and at moderate greenhouse temperatures, in an average of 75 to 85 days. The clone possesses to a high degree the desirable characteristics of hybrid vigor, great hardiness and disease resistance, its large flowers being produced on a single stalk. The clone is a virorous, good grower, and a good propagator as observed at Sandy, Oreg.

DESCRIPTION OF THE DRAWING

My new variety of lily plant is illustrated by the accompanying photographic drawing, which shows the upper end of a typical stem with a bud and three-quarter view of the flower in full bloom, the colors shown being as close to those herein specified as is reasonably possible to obtain by conventional photographic procedures.

DESCRIPTION OF THE NEW VARIETY

The following is a detailed description of my new variety of Asiatic hybrid lily with nomenclature according to The International Lily Register of The Royal Horticultural Society of London, England (Second Edition, 1969), and with color designations according to The R.H.S. Colour Chart published by The Royal Horticultural Society in 1966.

THE PLANT

Origin: Seedling.

Parentage:

- *Seed parent.*—Lilium 'Connecticut Red' (unpatented).
- *Pollen parent.*—Lilium 'Lovesong' (U.S. Plant Pat. No. 4,178).

Classification:

- *Horticultural.*—Upright Asiatic Hybrid Lily, Division I-A according to The Horticultural Classification of Lilies by The Royal Horticultural Society of London, England.
- *Commercial.*—Asiatic Lily Cultivar.

Form: Single stem, tall, erect and stately.

Height: About 100 to 120 cm. on stems produced by glasshouse forcing of bulbs of about 15 to 18 cm. in circumference with adequate light levels.

Growth: Vigorous and upright.

Foliage:

- *Quantity.*—Abundant.
- *Leaf size.*—About 8 to 14 cm. long and about 1 to 2 cm. wide.
- *Leaf shape.*—Lanceolate with acuminate tip.
- *Texture.*—Leathery.
- *Aspect.*—Glossy with light pubescence along the margins.
- *Color.*—Dark green, somewhat lighter on the lower side.

Bulbs:

- *Size.*—Various, depending on age, ranging to about 25 cm. in circumference in commercial use.
- *Color.*—White.

THE BUD

Form: Long, ovoid and obtuse.

Size: About 8 to 9 cm. long and about 5 cm. in circumference just prior to opening.

Opening rate: The bud opens slowly, in about one hour in response to morning light.

Color: Medium to deep red just prior to opening and as the tepals begin to unfurl.

Peduncle:

*Length.*—About 4 to 6 cm., in average, but may increase if light levels are too low or if bulbs have been improperly stored prior to forcing.

*Color.*—Dark green with light plum overlay.

THE FLOWER

Blooming habit: Once annually, blooming profusely in midseason for Asiatic lilies.

Size: The flowers are large, from 14 to 17 cm. in diameter.

Borne: As a single racemose inflorescence producing about 7 to 10 buds from a bulb having a circumference of about 12 to 15 cm.

Shape: Cup-shaped upon first opening then flattening somewhat as the tepals recurve during the second day.

Tepalage:

*Number.*—Six.

*Arrangement.*—Hexagonal and imbricated.

*Shape.*—Ovate with entire margins and with an acute tip.

*Appearance.*—Glossy.

*Color.*—The base color is red, 47A to 46B, and a red-orange, 33B, band about 1 cm. wide extends about 2 cm. from the nectaries. The nectaries are dark red overlaid with short, white pubescence.

*Tepal spotting.*—The basal third of each tepal is marked with a few tiny, relatively inconspicuous, dark magenta-purple spots just above the nectaries.

*Tepal longevity.*—The tepals stay on the stems about 3 weeks.

Pedicel:

*Length.*—Averaging about 5 to 15 cm.

*Form.*—Sturdy and ascending up to 45° from the horizontal and very rarely having secondary buds.

*Color.*—Dark green.

Fragrance: None.

Disease resistance: The flower and plant are resistant to disease and in particular, they are resistant to Botrytis blight and to Fusarium bulb rot.

Lasting quality: The flowers are long lasting both on the plant and as cut flowers.

THE REPRODUCTIVE ORGANS

Stamens:

*Number.*—Six.

*Arrangement.*—Typical of the genus Lilium.

*Anthers (dehisced) and Pollen.*—Color: Greyed orange, 171B.

*Filaments.*—Length: About 5 cm. Color: Soft red, 47C.

Pistils:

*Number.*—One.

*Length.*—About 5 cm.

*Stigma.*—Size: Small. Color: Soft red with deep plum overlay.

Character of ovary: Typical of genus Lilium.

THE FRUIT

Fertility: The fruit is fertile.

Shape: Ovoid.

Color at maturity: Soft brown, sometimes overlaid with soft plum.

This new lily variety most closely resembles the variety 'Red Night' but is distinguished by having larger flowers with broader tepals, a deep red color, without a brown undertone, and having a glossy tepal surface. The new variety has more and narrower leaves and is more reliable and uniform in its forcing performance.

I claim:

1. A new and distinctive Asiatic hybrid lily variety, substantially as herein shown and described, particularly characterized by its large, broad-tepalled, glossy flowers of rich deep red coloring and inconspicuous spotting; its vigorous growth and rapid natural propagation; the excellence of its flower form; and its versatility both as a garden plant and as a cut flower producer from precooled bulbs forced under glass.

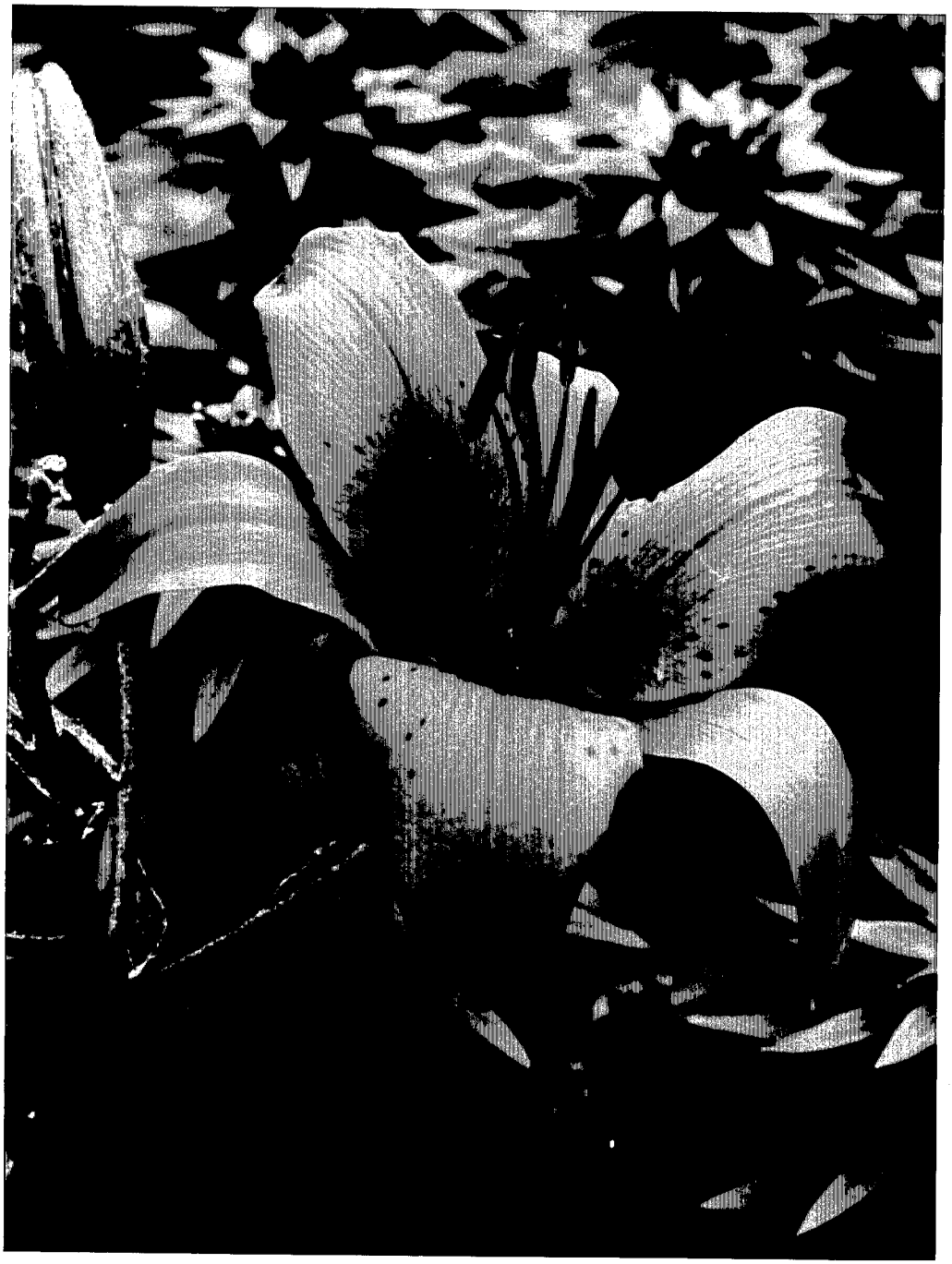

* * * * *